US008187265B2

(12) United States Patent
Choi et al.

(10) Patent No.: US 8,187,265 B2
(45) Date of Patent: May 29, 2012

(54) COAGULATION APPARATUS USING COLD PLASMA

(75) Inventors: Jun Choi, Pohang-si (KR); Jae Koo Lee, Pohang-si (KR); Kyong Tai Kim, Pohang-si (KR); Kyung Chul Woo, Pohang-si (KR); Jae Yoon Sim, Pohang-si (KR)

(73) Assignee: Postech Academy Industry Foundation, Pohang-Si (KR)

( * ) Notice: Subject to any disclaimer, the term of this patent is extended or adjusted under 35 U.S.C. 154(b) by 376 days.

(21) Appl. No.: 12/455,227

(22) Filed: May 29, 2009

(65) Prior Publication Data

US 2010/0130973 A1      May 27, 2010

(30) Foreign Application Priority Data

Nov. 25, 2008    (KR) .................. 10-2008-0117285

(51) Int. Cl.
*A61B 18/00* (2006.01)
(52) U.S. Cl. ................. 606/40; 606/27; 607/156
(58) Field of Classification Search ............ 606/40
See application file for complete search history.

(56) References Cited

U.S. PATENT DOCUMENTS

| 6,099,523 A | 8/2000 | Kim et al. |
| 6,887,339 B1 | 5/2005 | Goodman et al. |
| 2005/0256519 A1* | 11/2005 | Goble et al. .................. 606/34 |
| 2006/0081565 A1* | 4/2006 | Lee et al. ................ 219/121.43 |
| 2007/0225700 A1 | 9/2007 | Kuhner |

FOREIGN PATENT DOCUMENTS

| JP | 11-330837 A | 11/1999 |
| JP | 2002-537938 A | 11/2002 |
| JP | 2006-181353 A | 7/2006 |
| JP | 2008-539007 A | 11/2008 |

OTHER PUBLICATIONS

Extended European Search Report issued in European Patent Application No. 09160585.7-2305 on Apr. 12, 2010.
J Raiser and M Zenker, "Argon plasma coagulation for open surgical and endoscopic applications: state of the art", Published Aug. 4, 2006, 2006 IOP Publishing Ltd.

* cited by examiner

*Primary Examiner* — Michael Peffley
*Assistant Examiner* — Daniel Fowler
(74) *Attorney, Agent, or Firm* — Kile Park Goekjian Reed & McManus PLLC

(57) ABSTRACT

Provided is a coagulation apparatus using cold plasma. In the coagulation apparatus, the cold plasma is generated by a microwave resonator with low power consumption in the atmosphere, and the cold plasma is vented on a bleeding portion of a wound. Accordingly, it is possible to accelerate coagulation process, to reduce unfavorable side effect such as burns on the wound, and to efficiently sterilize the wound, simultaneously. In addition, it is possible to implement a small-sized portable coagulation apparatus.

5 Claims, 4 Drawing Sheets
(1 of 4 Drawing Sheet(s) Filed in Color)

COAGULATION APPARATUS USING COLD PLASMA

BACKGROUND OF THE INVENTION

1. Field of the Invention

The present invention relates to a coagulation apparatus using plasma, and more particularly, to a coagulation apparatus using a cold plasma which is generated by a microwave resonator with low power consumption in the atmosphere, wherein the cold plasma is vented on a bleeding portion of a wound, so that it is possible to accelerate coagulation process, to reduce unfavorable side effect such as burns on the wound, and to efficiently sterilize the wound, and it is possible to implement a small-sized portable coagulation apparatus.

2. Description of the Related Art

In general, various coagulation apparatuses are used so as to minimize bleeding during a surgical practice or bleeding caused from injury.

According to recent experiments, it has been known that plasma can be efficiently used for coagulation and wound healing due to plenty of reactive oxygen species (ROS), reactive nitrogen species, and hydrogen oxide as well as ions, electrons, electric field, and ultraviolet rays included in the plasma.

Among the various coagulation apparatuses, a coagulation apparatus using plasma generated from a gas has been widely used due to its high coagulation efficiency.

In the conventional coagulation apparatus using plasma, atmospheric pressure plasma is generated by using various power sources. Recently, a method for generating non-thermal plasma by using a microwave having a frequency of, for example, 900 MHz or 2.45 GHz with low power consumption has been researched and developed. Biomedical applications using plasma have been researched around the world. Skin care apparatuses for removing skin wrinkle or freckle have been used under US FDA approval.

Most of conventional plasma generating apparatuses using a microwave have excessively high power consumption of about 100 W or more due to magnetrons thereof. In addition, plasma generating apparatuses using a rectangular waveguide have a large volume and a complicated structure. Therefore, it is too difficult to implement a small-sized, portable coagulation apparatus with conventional concepts.

Recently, a coaxial microwave plasma torch using a discharge tube having an antenna structure has been proposed. However, the coaxial microwave plasma torch does not obtain a greater effect than the conventional plasma generating apparatuses using a rectangular waveguide. In addition, since a temperature of the plasma generated by the torch is too high, a harmful effect such as burns may occur. In addition, there is still a limitation to implement a smalls-sized coagulation apparatus.

SUMMARY OF THE INVENTION

The present invention is to provide a coagulation apparatus using cold plasma with a small-sized resonator which generates microwave to use the cold plasma in the atmosphere with low power consumption, capable of speedily coagulating blood of a wound and sterilizing the wound without an unfavorable side effect on the wound and capable of greatly reducing the entire volume of the coagulation apparatus.

The present invention is to provide a coagulation apparatus using cold plasma, wherein a microwave oscillation unit and an amplification unit are constructed with small-sized, light-weighted chip modules, and the chip modules are integrally coupled with a small-sized resonator, so that it is possible to implement a small-sized, portable coagulation apparatus using cold plasma.

According to an aspect of the present invention, there is provided a coagulation apparatus using cold plasma, comprising: a microwave oscillation unit having a signal source which generates a microwave signal for supplying a resonance energy used to generate the plasma; an amplification unit which is provided between the microwave oscillation unit and a resonator to amplify the microwave signal into an amplified microwave signal with a predetermined amplitude; the resonator which is driven by the resonance energy of the amplified microwave signal to generate the plasma by discharging an inert gas supplied by a gas supply unit; and a coagulation unit which is constructed with a hollow-tube venting unit which is connected to an end of the resonator to vent the plasma generated by the resonator, so that the cold plasma discharged and generated by the microwave signal can be concentrated on a bleeding portion to coagulate blood.

In the above aspect of the present invention, chip modules of the microwave oscillation unit and the amplification unit may be provided to the resonator, so that it is possible to implement a small-sized portable coagulation apparatus.

According to the present invention, since such a small-sized resonator for generating plasma with low power consumption is coupled with the microwave oscillation unit and the amplification unit, it is possible to implement a portable coagulation apparatus with a greatly-reduced volume, to reduce an unfavorable side effect such as burns on a wound due to exposure to the plasma, to accelerate coagulation process, and to sterilize the wound simultaneously.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features and advantages of the present invention will become more apparent by describing in detail exemplary embodiments thereof with reference to the attached drawings in which.

DETAILED DESCRIPTION OF THE INVENTION

Hereinafter, exemplary embodiments of the present invention are described in detail with reference to the accompanying drawings.

Figure 1:
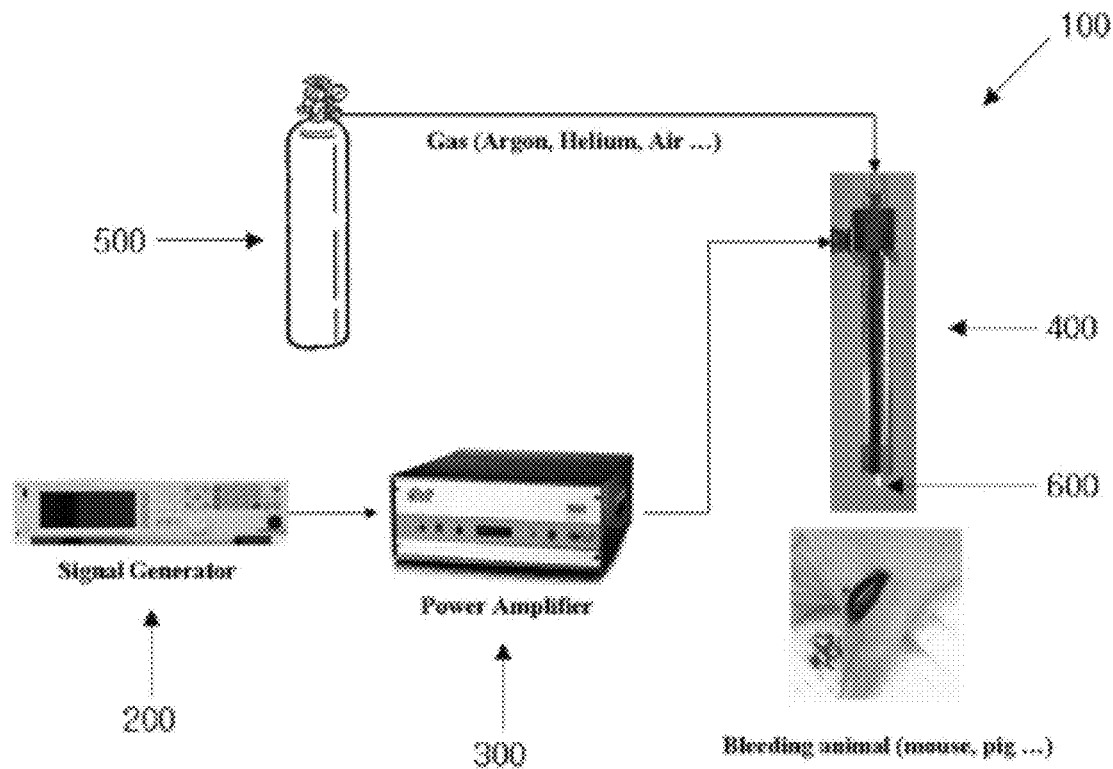
FIG. 1 is a view illustrating a construction of a coagulation apparatus using cold plasma according to the present invention.

FIG. 1 is a view illustrating a construction of a coagulation apparatus using cold plasma according to the present invention.

Figure 2:
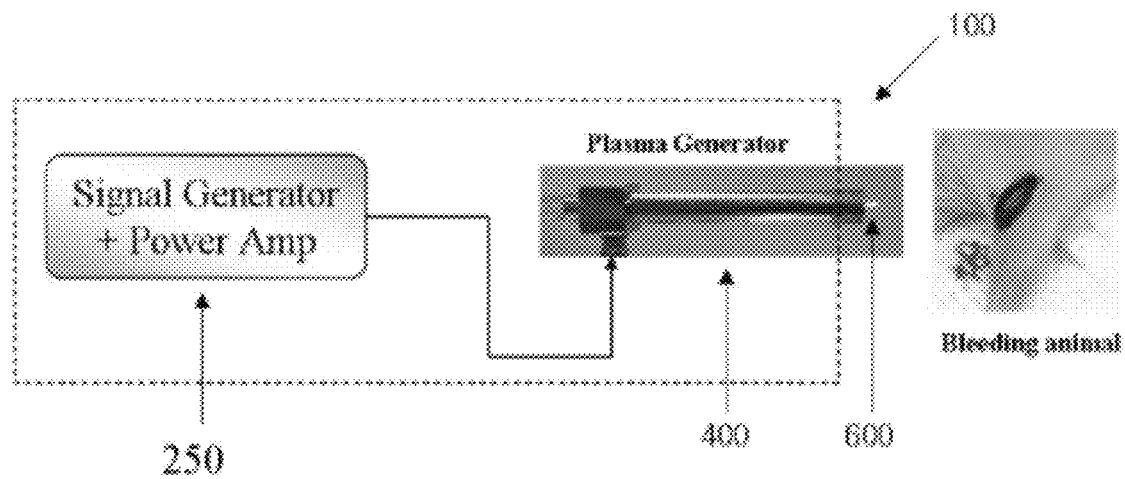
FIG. 2 is a view illustrating a construction of a portable resonator according to the present invention, where a microwave oscillation unit and an amplification unit are constructed with chip modules.

FIG. 2 is a view illustrating a construction of a portable resonator according to the present invention, where a microwave oscillation unit and an amplification unit are constructed with chip modules;

Referring to FIG. 1, a coagulation apparatus 100 using cold plasma according to the present invention includes: a microwave oscillation unit 200 which generates a microwave signal; an amplification unit 300 which amplifies the microwave signal into an amplified microwave signal with a predetermined amplitude; a resonator 400 which is driven by a resonance energy of the amplified microwave signal to generate plasma; a gas supply unit 500 which supplies an inert gas to the resonator; and a coagulation unit 600 which vents the plasma generated by the resonator to a bleeding portion.

The microwave oscillation unit 200 is constructed with a signal generator which generates a microwave by using a DC power supply unit supplying the resonance energy so as to generate the plasma with a low power. An output state of the microwave oscillation unit 200 is connected to the (power) amplification unit 300 which amplifies the generated microwave.

Preferably, the microwave generated by the microwave oscillation unit 200 has a frequency of 900 MHz or 2.45 GHz so as to supply resonance energy enough to generate the plasma.

The amplification unit 300 is provided between the output stage of the microwave oscillation unit 200 and the resonator 400 to amplify the microwave to a microwave having a sufficient amplitude and to supply the amplified microwave to a coaxial cable 410 through a second inner conductor 430 provided to the resonator 400.

Preferably, a DC-5V power supply which supplies a power voltage to the microwave oscillation unit 200 for generating the microwave and a DC-12V power supply which supplies a power voltage to the amplification unit 300 for amplifying the microwave are further included.

Alternatively, as shown in FIG. 2, small-sized, light-weighted chip modules 250 of the microwave oscillation unit and the amplification unit may be provided to the resonator 400, and a power supply unit constructed with batteries or the like may further be included. Therefore, it is possible to implement a portable coagulation apparatus 100 where all components except for the gas supply unit 500 (for supplying an inert gas to be ionized into plasma gas) can be implemented with a small size (for example, a palm size).

Figure 3:
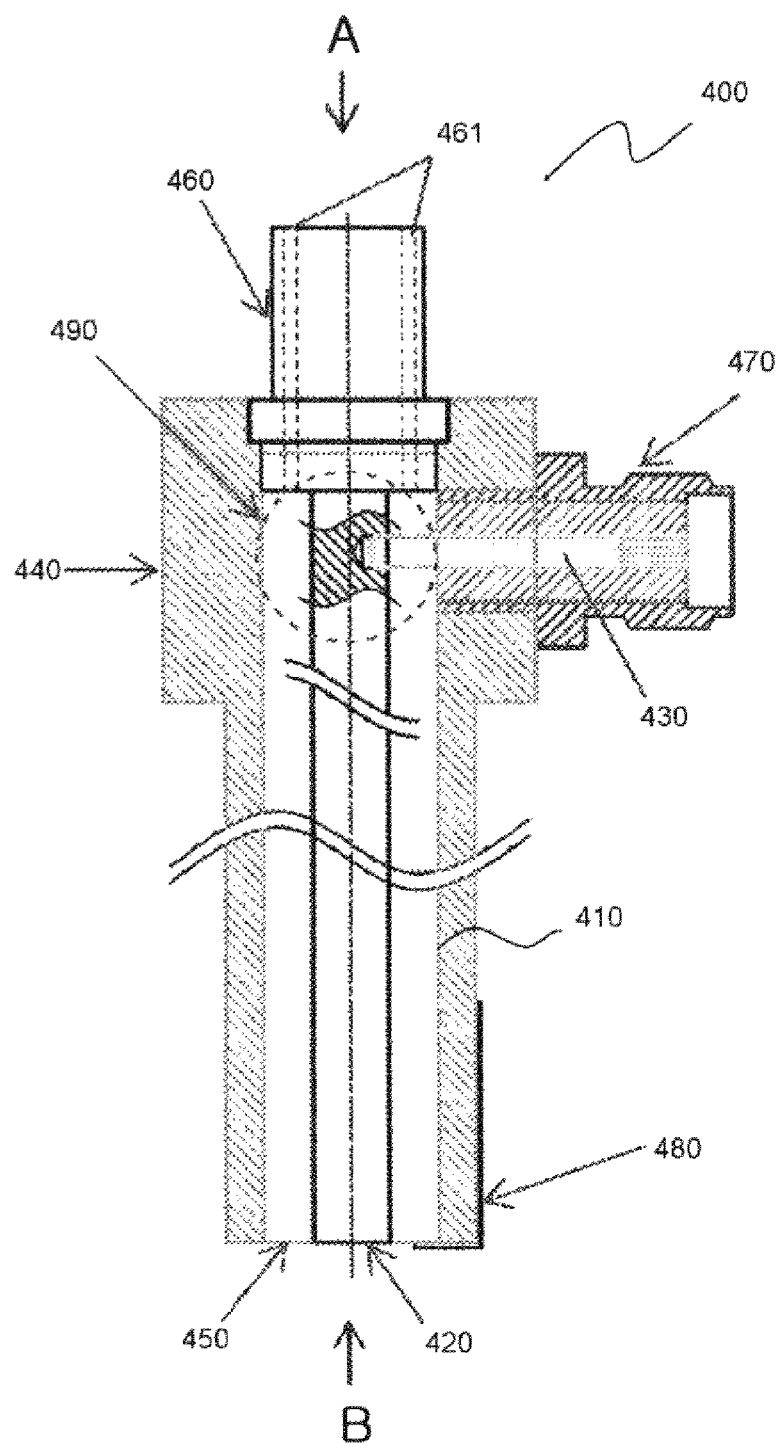
FIG. 3 is a cross-sectional view illustrating a resonator according to the present invention.

FIG. 3 is a cross-sectional view illustrating a resonator according to the present invention.

Referring to FIG. 3, the resonator 400 includes a coaxial cable 410, an outer conductor 440, a connection conductor 460, a connection member 470, and a discharge tip 480.

The coaxial cable 410 is constructed with a first inner conductor 420 and a dielectric material 450 which surrounds the first inner conductor 420. The coaxial cable 410 is surrounded with the outer conductor 440. The connection conductor 460 includes at least one gas injection tube 461. The connection conductor 460 is provided at one end of the coaxial cable 410 to electrically connect the first inner conductor 420 and the outer conductor 440.

The connection member 470 is constructed as an SMA connector so as to transmit to the coaxial cable 410 a microwave having a frequency of 900 MHz or 2.45 GHz which is generated by the microwave oscillation unit and amplified by the amplification unit. The connection member 470 includes a second inner conductor 430 which penetrates the outer conductor 440 to be electrically connected to the first inner conductor 420.

When the microwave is transmitted through the second inner conductor 430, the first inner conductor 420 of the coaxial cable 410 and the second inner conductor 430 of the connection member 470 are connected to each other at a coupling portion 490, so that a microwave having a TEM (transverse electromagnetic) mode can be transmitted to the coaxial cable 410. At this time, the connection member 470 is to be electrically connected to the outer conductor 440 which surrounds the coaxial cable 410 and the first inner conductor 420 which is included in the inner portion of the coaxial cable 410. Preferably, an insulating material is provided between the second inner conductor 430 and the connection member 470.

The discharge tip 480 is attached to the other end of the coaxial cable 410 so as to minimize power consumption of the coaxial cable 410 for generating plasma.

In this manner, the resonator 400 generates the plasma by using the resonance energy of the microwave having a frequency of 900 MHz or 2.45 GHz which is applied through the second inner conductor 430. The connection member 470, the connection conductor 460, the outer conductor 440, the first inner conductor 420, and the second inner conductor 430 are electrical connected so as to collectively perform resonance.

In addition, the microwave applied to the coaxial cable 410 is a TEM wave. A TEM wave has no electric and magnetic fields in the propagation direction but it has electric and magnetic field in a direction perpendicular to the propagation direction, so that electromagnetic energy can be transmitted by the TEM wave.

Preferably, air can be used as a dielectric material filling a space between the first inner conductor 420 and the outer conductor 440 in the coaxial cable 410. Accordingly, the inert gas flown through the gas injection tube 461 into the air space can be flown toward the end portion of the coaxial cable 410.

Namely, since the air space as a dielectric material is an empty space, the inert gas to generate the plasma can be injected into the space without any significant perturbation of the resonator behavior. Due to the resonance energy of the conductors applied with the microwave, the injected gas turns into plasma. Next, the plasma is flown toward a lower portion of the resonator 400.

A length of the coaxial cable 410 is designed to be ¼ or ¾ of a wavelength λ of the microwave or a multiple thereof, that is, $(2n-1)\lambda/4$ (n=1, 2, 3 . . . ) so as to efficiently generate resonance with the microwave. Preferably, the length of the coaxial cable 410 is designed to be the shortest length, that is, ¼ of the wavelength λ of the microwave to minimize energy loss in the coaxial cable 410. When the above condition of the length of the coaxial cable 410 is satisfied, a maximum of electric field intensity is formed at the end of the resonator 400, so that the plasma can be easily generated at atmospheric pressure by using the maximum electric field intensity.

In a case where the frequency of the microwave is 900 MHz, ¼ of the wavelength λ of the microwave becomes 8.33 cm according to a relationship among a frequency, a wavelength, and a velocity of light. Therefore, the length of the resonator 400 can be less than 10 cm, so that it is possible to manufacture a small-sized portable resonator. Similarly, in a case where the frequency of the microwave is 2.45 GHz, ¼ of the wavelength λ of the microwave becomes 3.06 cm. Therefore, the length of the resonator 400 can be less than 5 cm.

As the coaxial cable 410 is seen from the coupling portion 490 between the first inner conductor 420 of the coaxial cable 410 and the second inner conductor 430 of the connection member 470, input impedance of the coaxial cable 410 varies with a position of the coupling portion 490. Therefore, self-impedance can be controlled by adjusting the position of the connection member 470. As a result, it is possible to easily obtain impedance matching between the resonator 400 and the microwave oscillation unit 200 which applies the microwave signal through the second inner conductor 430 to the coaxial cable 410 or impedance matching between the resonator 400 and the amplification unit 300 which amplifies the microwave signal output from the microwave oscillation unit 200. Accordingly, a separate matching network is not necessary for the resonator 400, and thus, the entire volume of a coagulation apparatus can be reduced, so that a portable coagulation apparatus can be implemented.

In order to generate plasma at atmospheric pressure, a high electric field intensity having $10^6$ V/m or higher is needed. Therefore, the discharge tip 480 is used so as to ignite the plasma by partially increasing the electric field at the open end of the resonator. After the plasma is generated by the occurrence of discharge, the discharge tip 480 may not necessarily be operated. Therefore, the discharge tip 480 may be operated when the discharge tip 480 is needed, but it may be removed from the resonator 400 when the discharge tip 480 is not needed.

In this case, the discharge tip 480 is constructed to be fastened to the outer conductor 440 by using a spring. When the discharge tip 480 is needed, the discharge tip 480 instantaneously approaches the first inner conductor 420 so as to increase the electric field intensity at the end of the coaxial cable 410, thereby discharging the plasma. Accordingly, the resonator 400 can generate the plasma with low power consumption of about 5 W or less using argon gas at atmospheric pressure.

Figure 4:
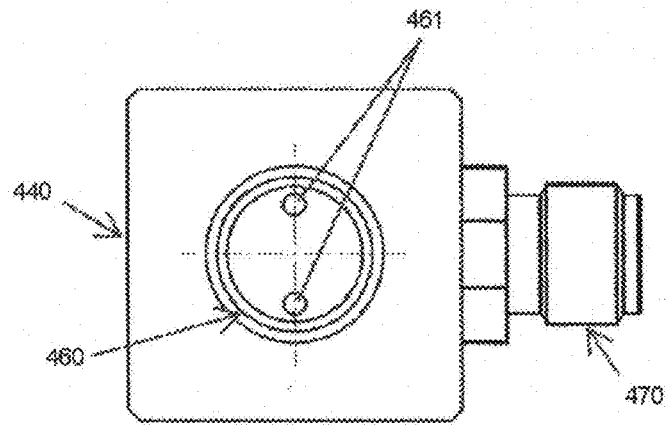
FIG. 4 is a cross-sectional view taken in the direction A of FIG. 3.
Figure 5:
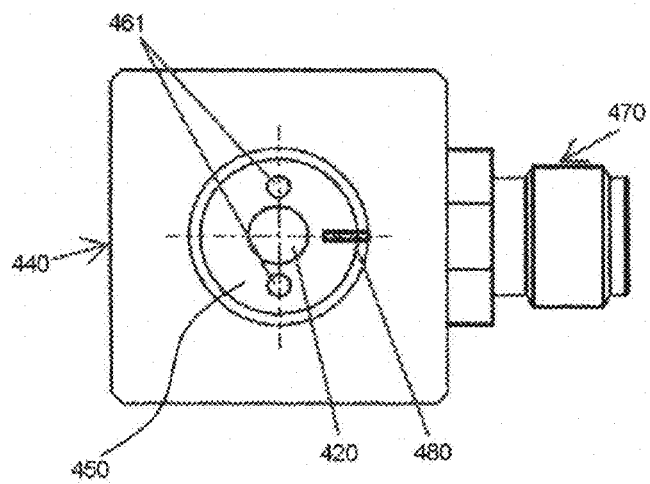
FIG. 5 is a cross-sectional view taken in the direction B of FIG. 3.

FIG. 4 is a cross-sectional view taken in the direction A of the resonator shown in FIG. 3. FIG. 5 is a cross-sectional view taken in the direction B of the resonator shown in FIG. 3.

Referring to FIGS. 4 and 5, the connection conductor 460 is inserted into a central portion of the outer conductor 440, and two gas injection tubes 461 are provided to the connection conductor 460. Although the inert gas is flown into the dielectric material 450 through the two gas injection tubes 461 in the figures, one gas injection tube 461 may be provided. The inert gas flown through the gas injection tube 461 may be helium or argon which is stored in the gas supply unit 500 such as a gas container connected to the gas injection tubes 461.

The outer conductor 440 surrounds one end portion of the coaxial cable 410, and the first inner conductor 420 is provided at the central portion of the coaxial cable 410. The dielectric material 450 is provided between the outer surface of the coaxial cable 410 and the first inner conductor 420 thereof. The discharge tip 480 is provided on an end surface B of coaxial cable 410, so that the plasma is discharged from the end surface B of the coaxial cable 410.

The coagulation unit 600 is constructed with a hollow-tube venting unit which is connected to one end of the coaxial cable 410 to vent the plasma generated by the resonator 400. Due to the coagulation unit 600, the cold plasma discharged by using the microwave can be concentrated on a bleeding portion of a wound so as to accelerate coagulation process and to sterilize the wound, simultaneously.

Now, a coagulation treatment by the coagulation apparatus using cold plasma according to the present invention will be described.

In the above resonator 400 having a simple, portable structure, the microwave having a frequency of 900 MHz or 2.45 GHz which is generated by the microwave oscillation unit 200 and amplified by the amplification unit 300 is transmitted to the coaxial cable 410 through the second inner conductor 430 of the connection member 470.

Argon gas which is stored in the gas supply unit 500 is flown through the gas injection tube 461 of the connection conductor 460 into an air space with air as a dielectric material between the outer surface of the coaxial cable 410 and the first inner conductor 420. Instead of the argon gas, helium gas or other inert gases can be used. In addition, two or more types of the inert gases can be supplied through various types or shapes of the gas injection tubes.

The length of the coaxial cable 410 is designed to be ¼ or ¾ of a wavelength λ of the microwave or a multiple thereof, that is, $(2n-1)\lambda/4$ ($n=1, 2, 3 \ldots$) so as to efficiently generate resonance with the microwave. Accordingly, a maximum of electric field intensity is formed at the end of the resonator 400, so that the plasma can be easily generated by using the maximum electric field intensity.

Unlike a conventional coagulation apparatus using plasma, the coagulation apparatus according to the present invention has low power consumption of about 5 W or less at atmospheric pressure.

Figure 6:
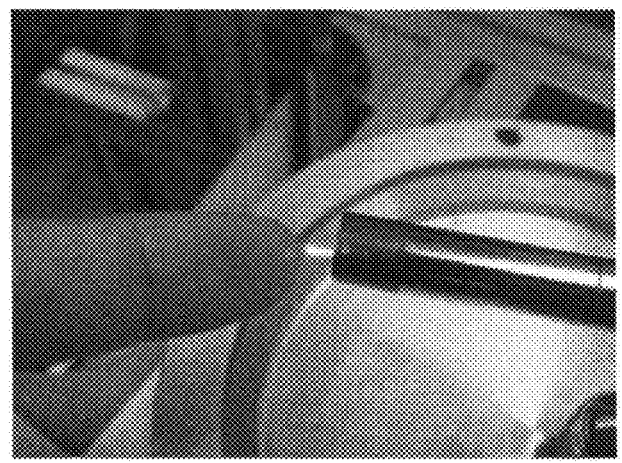
FIG. 6 is a photograph illustrating that a human body is in contact with cold plasma generated according to the present invention.

FIG. 6 is a photograph illustrating that a human body is in contact with cold plasma generated according to the present invention.

Figure 7:
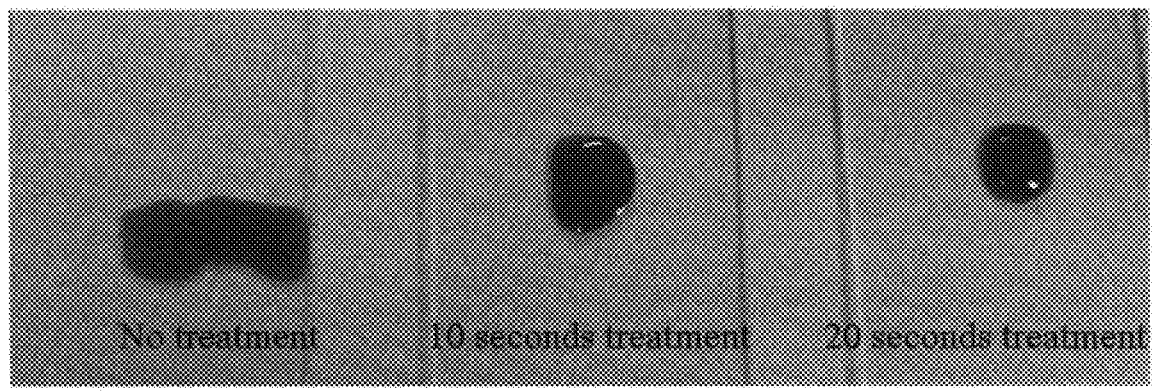
FIG. 7 is a photograph illustrating comparison of a degree of coagulation of blood which is not treated with cold plasma with a degree of coagulation of blood which is treated with cold plasma generated according to the present invention.

Referring to FIG. 6, it can be understood that a temperature of the plasma generated by the coagulation apparatus is so low that a human body is not harmed by directly contacting with the plasma vented from the coagulation unit 600. Since such low temperature plasma (cold plasma) is vented on the bleeding portion of the wound, unfavorable side effect such as burns on the wound can be reduced, and coagulation and sterilization can be efficiently performed. FIG. 7 is a photograph illustrating comparison of a degree of coagulation of blood which is not treated with cold plasma with a degree of coagulation of blood which is treated with cold plasma generated according to the present invention.

Referring to FIG. 7, it can be understood that the blood which is not treated with cold plasma generated by the coagulation apparatus according to the present invention cannot be easily coagulated but it spreads. In this experiment, blood of a mouse is used.

On the contrary, it can be understood that, if the blood is treated in vitro for 10 or 20 seconds with the cold plasma generated by the coagulation apparatus according to the present invention, the blood can be easily coagulated by the short-time treatment. In this experiment, low power consumption of 4 W is used for generating the cold plasma, and an amount (flow rate) of the argon gas used for about 10 to 20 seconds is 3 lpm (liter per minute).

Figure 8:
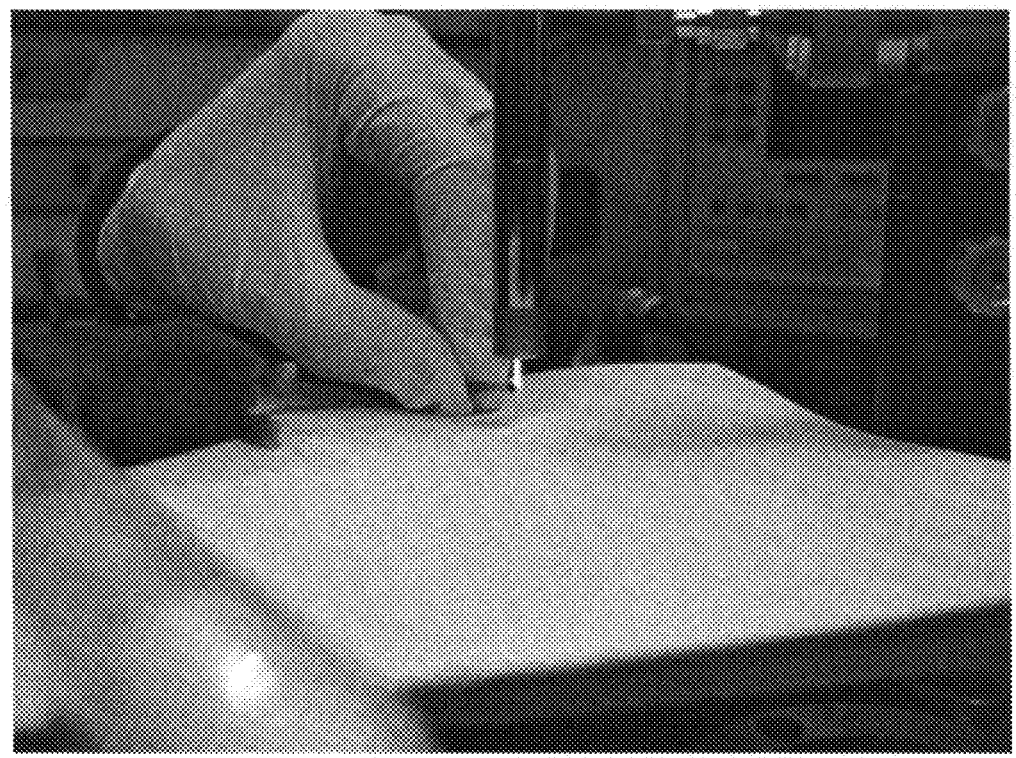
FIG. 8 is a photograph illustrating that bleeding in a tail of a mouse is stopped by a treatment with cold plasma according to the present invention.

FIG. 8 is a photograph illustrating that bleeding in a tail of a mouse is stopped by a treatment with cold plasma according to the present invention. In the experiment, bleeding is made at a tail of a living mouse, and the bleeding is treated in vivo with the cold plasma generated according to the present invention.

In general, in case of not using a plasma treatment, a time of about five minutes is taken to coagulate blood. However, it can be understood that, in case of venting cold plasma generated by a coagulation apparatus 100 using a simple, small-sized resonator 400 with low power consumption according to the present invention, a time of one to two minutes or less is taken to coagulate blood. In this experiment, low power consumption of 3.5 W is used for generating the cold plasma, and an amount (flow rate) of the argon gas used for about 10 to 20 seconds is 3 l pm (liter per minute).

A conventional coagulation apparatus has a complicated structure with high power consumption for generating atmospheric pressure plasma. High-temperature plasma vented by the coagulation apparatus causes an unfavorable side effect such as burns on a bleeding portion. However, the coagulation apparatus using cold plasma according to the present invention has a simple structure, in which a small-sized portable resonator generates atmospheric pressure cold plasma with low power consumption. By venting the cold plasma on the bleeding portion, it is possible to accelerate coagulation process without an unfavorable side effect and to sterilize the wound, simultaneously.

While the present invention has been shown and described in connection with the exemplary embodiments, it will be apparent to those skilled in the art that modifications and variations can be made without departing from the spirit and scope of the invention as defined by the appended claims.

What is claimed is:

1. A coagulation apparatus using cold plasma, comprising:
    a microwave oscillation unit having a signal source which generates a microwave signal for supplying a resonance energy used to generate the plasma;
    an amplification unit which is provided between the microwave oscillation unit and a resonator to amplify the microwave signal into an amplified microwave signal with a predetermined amplitude;
    the resonator which is driven by the resonance energy of the amplified microwave signal to generate the plasma by discharging an inert gas supplied by a gas supply unit; and
    a coagulation unit which is constructed with a hollow-tube venting unit which is connected to an end of the resonator to vent the plasma generated by the resonator, so that the cold plasma discharged and generated by the microwave signal can be concentrated on a bleeding portion to coagulate blood,
    wherein the resonator comprises:
    a coaxial cable which is constructed with a first inner conductor and a dielectric material which surrounds the first inner conductor;
    an outer conductor which surrounds the coaxial cable;
    a connection conductor which has at least one gas injection tube and which is provided at one end of the coaxial cable to electrically connect the first inner conductor and the outer conductor; and
    a connection member which has a second inner conductor which penetrates the outer conductor to be electrically connected to the first inner conductor.

2. The coagulation apparatus using cold plasma according to claim 1,
    wherein the microwave oscillation unit and the amplification unit include chip modules, and the chip modules are provided to the resonator.

3. The coagulation apparatus using cold plasma according to claim 1, wherein the microwave signal which is generated by the microwave oscillation unit and transmitted through the second inner conductor to the coaxial cable has a frequency of 900 MHz or 2.45 GHz.

4. The coagulation apparatus using cold plasma according to claim 1, wherein a length of the coaxial cable is designed to be ¼ or ¾ of a wavelength of the microwave signal so as to form a maximum electric field intensity at the end of the resonator, so that the plasma discharge occurs with low power consumption of about 5 W or less in the atmosphere.

5. The coagulation apparatus using cold plasma according to claim 4, wherein in a case where the frequency of the microwave siganl is 900 MHz, the length of the resonator becomes about 10 cm, and in a case where the frequency of the microwave signal is 2.45 GHz, the length of the resonator becomes about 3 cm.

* * * * *